United States Patent [19]

Kelman

[11] Patent Number: 4,465,470

[45] Date of Patent: Aug. 14, 1984

[54] APPARATUS FOR AND METHOD OF IRRIGATING AND ASPIRATING AN EYE

[76] Inventor: Charles D. Kelman, 269-70 Grand Central Pkway., Floral Park, N.Y. 11005

[21] Appl. No.: 385,010

[22] Filed: Jun. 4, 1982

[51] Int. Cl.³ .............................................. A61M 1/00
[52] U.S. Cl. ........................................ 604/27; 604/28
[58] Field of Search ...................... 604/19, 22, 28, 30, 604/32–35, 39, 40, 43, 48, 49, 51, 54, 65, 80, 93, 94, 118, 119, 131, 149, 150, 257, 258, 262, 27

[56] References Cited

U.S. PATENT DOCUMENTS

| | | | |
|---|---|---|---|
| 3,812,855 | 5/1974 | Banko | 604/31 |
| 4,007,742 | 2/1977 | Banko | 604/65 |
| 4,180,074 | 12/1979 | Murry et al. | 604/118 |
| 4,184,491 | 1/1980 | McGannon | 604/28 |

FOREIGN PATENT DOCUMENTS 459369  7/1979  U.S.S.R. ................................ 604/30

OTHER PUBLICATIONS

"Phacoemulsification and Aspiration Course", Kelman, M.D., pp. 4, 28, 38, 39.

*Primary Examiner*—C. Fred Rosenbaum
*Assistant Examiner*—J. L. Kruter
*Attorney, Agent, or Firm*—Henry Sternberg

[57] ABSTRACT

Apparatus for and method of irrigating and aspirating an eye utilizing valves in a conduit and conduit branches to control the flow of fluid into and out of the eye under the force of gravity.

13 Claims, 1 Drawing Figure

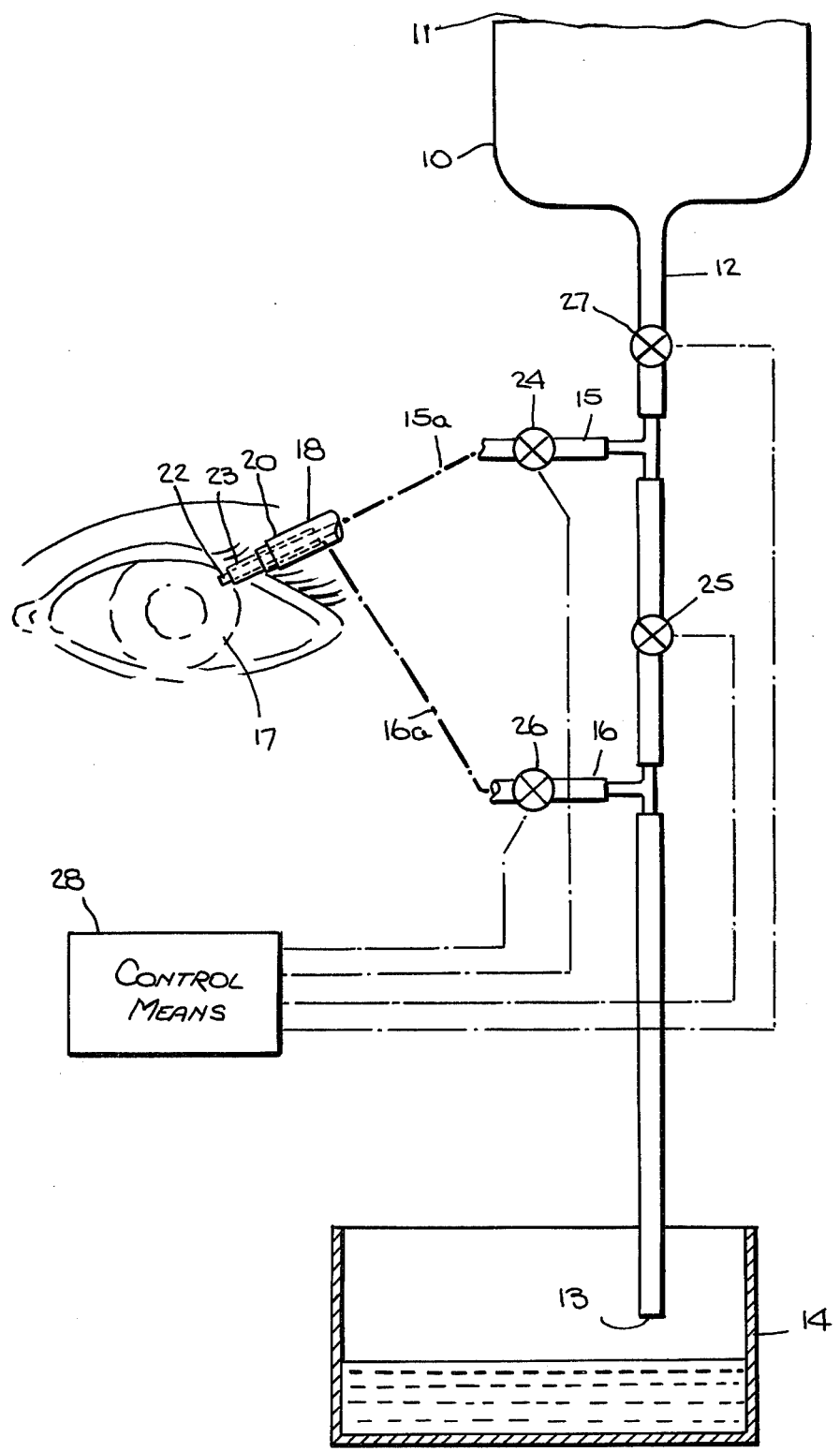

APPARATUS FOR AND METHOD OF IRRIGATING AND ASPIRATING AN EYE

This invention relates to apparatus for and a method of irrigating and aspirating an eye.

Prior apparatus for irrigating and aspirating an eye is known which is of relatively complex construction and utilizes a vacuum pump to perform the aspiration function.

It is an object of the present invention, therefore, to provide a new and improved apparatus for and method of irrigating and aspirating an eye.

It is another object of the invention to provide a new and improved apparatus for irrigating and aspirating an eye which is of relatively simple construction and is easily operated.

In accordance with the invention, apparatus for irrigating and aspirating an eye comprises a fluid container adapted to be disposed at an elevation higher than the elevation of the eye. The apparatus also includes a fluid conduit extending from the fluid container to an open end disposed at an elevation lower than the elevation of the eye. The conduit has two spaced conduit branches along the conduit for insertion in the eye. The apparatus includes first valve means in a first of the conduit branches for controlling fluid flow through the first conduit branch. The apparatus also includes second valve means in the conduit between the conduit branches for controlling fluid flow through the conduit between the conduit branches. The apparatus also includes third valve means in the second of the conduit branches for controlling fluid flow through the second conduit branch. The apparatus also includes means for individually opening and closing the valve means for priming the apparatus, for irrigating the eye, and for irrigating and aspirating the eye.

Also in accordance with the invention, a method of irrigating and aspirating an eye comprises disposing a fluid container at an elevation higher than the elevation of the eye and inserting in the eye two fluid conduit branches spaced along a fluid conduit extending from the fluid container to an open end. A first of the conduit branches has first valve means in the first conduit branch for controlling fluid flow through the first conduit. The fluid conduit has second valve means in the conduit between the conduit branches for controlling fluid flow through the conduit between the conduit branches. The fluid conduit has third valve means in the second conduit branch for controlling fluid flow through the second conduit branch. The method also includes disposing the open end of the conduit at an elevation lower than the elevation of the eye. The method also includes individually opening and closing the valve means for priming the fluid conduit and conduit branches, for irrigating the eye, and for irrigating and aspirating the eye.

For a better understanding of the present invention, together with other and further objects thereof, reference is made to the following description, taken in connection with the accompanying drawing, and its scope will be pointed out in the appended claims.

Referring now to the drawing:

The figure is a schematic view of apparatus for irrigating and aspirating an eye, constructed in accordance with the invention.

Referring now more particularly to the figure, apparatus for irrigating and aspirating an eye comprises a fluid container adapted to be disposed at an elevation higher than the elevation of the eye, perferably approximately 24 inches above the elevation of the eye. The fluid container may, for example, be a glass or plastic container 10 containing an eye irrigation solution 11 which may, for example, be an artificial aqueous or balanced salt solution. The apparatus includes a fluid conduit 12 extending from the fluid container to an open end 13 disposed at an elevation lower than the elevation of the eye. The fluid conduit 12 may be of any suitable plastic material. The open end 13 may drain into, for example, a container 14. The fluid conduit 12 has two spaced conduit branches 15, 16 along the conduit 12 for insertion in an eye 17 through a suitable corneal-scleral incision. As represented by broken lines 15a, 16a, the conduits 15 and 16 include a conventional irrigation/aspiration hand piece 18, with an irrigation-/aspiration tip cap 20 and irrigation/aspiration tips 22, 23, all of conventional construction which may be of a type used in the Cavitron E.I.S., Model 6500, manufactured by Cavitron Surgical Systems, division of Syntel, Inc., Irvine, Calif. The tip 22 is an inner irrigation open metal tube within an outer aspiration open plastic sleeve 23 which has an aperture (not shown) in its side near the open end of the sleeve 23. The tubing of the conduit 12 and the conduit branches 15, 16 may, for example, be pliable silastic tubing similar to the type used in the Cavitron E.I.S. Model 6500.

The apparatus also includes first valve means in a first of the conduit branches 15 for controlling fluid flow through the first conduit branch. This valve means may, for example, be a solenoid valve 24 of conventional construction, which may be manually operable if desired. The apparatus also includes second valve means 25 in the conduit between branches 15, 16 for controlling fluid flow through the conduit 12 between the conduit branches 15, 16. The apparatus also includes third valve means 26 in the second of the conduit branches 16 for controlling fluid flow through the second conduit branch 16. The apparatus preferably also includes fourth valve means 27 in the conduit 12 between the container 10 and both of the conduit branches 15, 16 for controlling fluid flow out of the fluid container. All these valve means may be similar to the valve means 24.

The apparatus also includes means for individually opening and closing the valve means and for priming the apparatus, for irrigating the eye, and for irrigating and aspirating the eye. This means comprises, for example, an electrical control means of conventional construction, which may have individual switches (not shown) for individually controlling the energization of the solenoid valves 24, 25, 26 and 27. These switches may be manually operable or may be controlled by a suitable timer. The construction of the control means is not shown in detail as it is obvious to one skilled in the art.

The open end of the conduit 12 preferably is approximately thirty inches below the elevation of the eye to provide aspiration of the eye.

The irrigation/aspiration tips 22, 23 preferably are inserted into the eye with the solenoid valve 27 closed. The solenoid valves 24, 25, 26 may be open or closed.

In order to fill conduit 16 in the region 16a with fluid, prior to inserting the irrigation/aspiration tips 22,23 in the eye, a removable cap (not shown) may be placed over the open ends of the irrigation/aspiration tips 22,23 and the solenoid valves 24,26 may be opened under the control of the control means 28 while the solenoid valve 27 is open and the solenoid valve 25 is closed. Fluid then flows from the container 10 through the open solenoid valve 27, the conduit 15, the open solenoid valve 24, the conduit region 15a, inside the cap enclosing together the open ends of the irrigation/aspiration tips 22,23, out the conduit region 16a, the solenoid valve 26, the conduit 16, and the open end 13 of the conduit 12 under the force of gravity. Solenoid valves 24 and 26 may then be closed under the control of the control means 28. The cap may then be removed from the irrigation/aspiration tips 22,23.

Under the control of the control means 28, to prime the fluid conduit 12 and the conduit branches 15, 16, the control means 28 maintains solenoid valves 24 and 26 closed and then the control means 28 opens solenoid valve 25 while solenoid valve 27 remains open. Fluid from the container 10 flows through the open solenoid valves 27 and 25 and out through the open end 13 of the conduit 12 under the force of gravity. This flow primes the apparatus.

To irrigate the eye, the control means 28 opens solenoid valve 24 and closes solenoid valve 25 while solenoid valve 27 remains open and solenoid valve 26 remains closed. Fluid flows through conduit 12, solenoid valve 27, conduit branch 15, solenoid valve 24, and irrigation tip 22 into the eye under the force of gravity.

To irrigate and aspirate the eye, the control means 28 opens solenoid valve 26 while solenoid valve 27 and 24 remain open and solenoid valve 25 remains closed. Fluid continues to flow into the eye through irrigation tip 22 as previously described. Fluid then flows out of the eye though aspiration tip 23, conduit branch 16, solenoid valve 26 and conduit 12 to the open end 13 under the force of gravity.

In this way it is possible easily and without costly apparatus (i.e. no pump) to control the amount of fluid and thus the fluid pressure in the eye. It is, of course, important for the fluid pressure in the eye not to become excessive and by use of the gravity feed and gravity discharge apparatus and method according to this invention, a safe irrigation/aspiration procedure is possible. The surgeon using the apparatus can, by varying the height of the container 10, vary the flow rate of the fluid into the eye and thus vary the fluid pressure in the eye.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Apparatus for irrigating and aspirating an eye, utilizing gravity flow, comprising:
    a fluid container containing irrigation fluid disposed at an elevation higher than the elevation of the eye;
    a fluid conduit having an open end and extending from said fluid container to said open end disposed at and terminating at an elevation lower than the elevation of the eye, said conduit having two spaced conduit branch means along said conduit for supply and removal of fluid from the eye;
    first valve means in a first of said two spaced conduit branch means for controlling fluid flow through said first conduit branch means;
    second valve means in said conduit between said two spaced conduit branch means for controlling fluid flow through said conduit between said conduit branch means;
    third valve means in the second of said conduit branch means for controlling fluid flow through said second conduit branch means; and
    means for individually opening and closing said valve means for priming the apparatus with fluid from the fluid container, for irrigating the eye, and for irrigating and aspirating the eye whereby priming of the apparatus, and irrigation and aspiration of the eye is accomplished without any external pump source other than the gravity flow of the fluid in the conduit.

2. Apparatus in accordance with claim 1 which includes fourth valve means in said conduit between said container and both of said conduit branch means for controlling fluid flow out of said fluid container.

3. Apparatus in accordance with claim 2 in which said means for opening and closing said valve means opens said fourth valve means.

4. Apparatus in accordance with claim 1 in which said means for opening and closing said valve means closes said first and third valve means and opens said second valve means for priming the apparatus.

5. Apparatus in accordance with claim 1 in which said means for opening and closing said valve means opens said first valve means and closes said second and third valve means for irrigating the eye.

6. Apparatus in accordance with claim 1 in which said means for opening and closing said valve means opens said first and third valve means and closes said second valve means for irrigating and aspirating the eye.

7. Apparatus in accordance with claim 1 in which said open end of said conduit is approximately thirty inches below the elevation of the eye.

8. Apparatus in accordance with claim 1 in which said fluid container is disposed approximately 24 inches above the elevation of the eye.

9. A method of irrigating and aspirating an eye comprising:
    disposing a fluid container containing irrigation fluid at an elevation higher than the elevation of the eye;
    positioning a fluid conduit with one open end communicating with the fluid in said container and a second open end disposed at an elevation lower than the elevation of said eye;
    inserting a handpiece into the eye; opening a fluid passage between the fluid container and the handpiece via said conduit and one of a pair of fluid conduit branches spaced along said conduit for allowing fluid to flow by gravity into the eye to irrigate the eye;
    opening a second fluid passage between the handpiece and the open end of said conduit via said conduit and the other of said pair of conduit branches spaced along said conduit at said elevation lower than the elevation of the eye for permitting fluid from the eye to flow by gravity to said lower elevation to aspirate the eye; and
    closing a fluid passage in said conduit between said pair of conduit branches.

10. A method of irrigating and aspirating an eye in accordance with claim 9 in which said fluid conduit and both of said conduit branches have valve means and which method includes selectively opening and closing said valve means for controlling fluid flow through said conduit and through said conduit branches.

11. A method of irrigating and aspirating an eye comprising:
- disposing a fluid container at an elevation higher than the elevation of the eye;
- disposing the open end of a fluid conduit extending from the fluid container at an elevation lower than the elevation of the eye, said fluid conduit having two spaced conduit branches along said conduit for insertion in the eye;
- inserting said conduit branches in the eye;
- closing first valve means in a first of said conduit branches for controlling fluid flow through said first conduit branch;
- closing third valve means in the second of said conduit branches for controlling fluid flow through said second conduit branch;
- opening second valve means in said conduit between said conduit branches for controlling fluid flow through said conduit between said conduit branches, thereby priming apparatus for irrigating and aspirating the eye.

12. A method of irrigating an eye comprising:
- disposing a fluid container at an elevation higher than the elevation of the eye;
- disposing the open end of a fluid conduit extending from the fluid container at an elevation lower than the elevation of the eye, said fluid conduit having two spaced conduit branches along said conduit for insertion in the eye;
- inserting said conduit branches in the eye;
- opening first valve means in a first of said conduit branches for controlling fluid flow through said first conduit branch;
- closing third valve means in the second of said conduit branches for controlling fluid flow through said second conduit branch;
- closing second valve means in said conduit between said conduit branches for controlling fluid flow through said conduit between said conduit branches, thereby irrigating the eye.

13. A method of irrigating and aspirating an eye comprising:
- disposing a fluid container at an elevation higher than the elevation of the eye;
- disposing the open end of a fluid conduit extending from the fluid container at an elevation lower than the elevation of the eye, said fluid conduit having two spaced conduit branches along said conduit for insertion in the eye;
- inserting said conduit branches in the eye;
- opening first valve means in a first of said conduit branches for controlling fluid flow through said first conduit branch;
- opening third valve means in the second of said conduit branches for controlling fluid flow through said second conduit branch;
- closing second valve means in said second conduit between said conduit branches for controlling fluid flow through said conduit between said conduit branches, thereby irrigating and aspirating the eye.

* * * * *